US 9,381,513 B2

(12) United States Patent
Chien et al.

(10) Patent No.: US 9,381,513 B2
(45) Date of Patent: *Jul. 5, 2016

(54) DETECTION CHIP AND METHOD FOR USING THE SAME

(71) Applicant: Industrial Technology Research Institute, Hsinchu (TW)

(72) Inventors: Liang-Ju Chien, Kaohsiung (TW); Yu-Ying Lin, Tainan (TW); Chi-Han Chiou, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,289

(22) Filed: Mar. 21, 2014

(65) Prior Publication Data

US 2015/0011438 A1     Jan. 8, 2015

(30) Foreign Application Priority Data

Jul. 4, 2013 (TW) ................. 102124053

(51) Int. Cl.
    *B01L 3/00* (2006.01)
    *B01F 13/00* (2006.01)
    *C12Q 1/68* (2006.01)

(52) U.S. Cl.
    CPC ....... *B01L 3/502792* (2013.01); *B01F 13/0071* (2013.01); *B01L 3/50273* (2013.01); *C12Q 1/686* (2013.01); *B01L 2200/0647* (2013.01); *B01L 2200/0673* (2013.01); *B01L 2200/16* (2013.01); *B01L 2300/0816* (2013.01);
    (Continued)

(58) Field of Classification Search
    CPC .......... B01L 3/502792; B01L 3/50273; B01L 2200/0647; B01L 2300/0816; B01L 2300/0867; B01L 2200/16; B01L 2400/043; B01L 2400/0427; B01L 2300/161; B01L 2200/00; C12Q 1/686; B01F 13/0071; Y10T 436/2575

See application file for complete search history.

(56) References Cited

U.S. PATENT DOCUMENTS 5,350,676 A    9/1994 Oberhardt et al.
5,601,991 A    2/1997 Oberhardt
(Continued)

FOREIGN PATENT DOCUMENTS

CN    2864677    1/2007
CN    101171521    4/2008
(Continued)

OTHER PUBLICATIONS

David Mabey, et al, "Diagnostics for the Developing World," Nature Reviews Microbiology, vol. 2, Mar. 2004, pp. 231-240.
(Continued)

*Primary Examiner* — Lore Jarrett
(74) *Attorney, Agent, or Firm* — Jianq Chyun IP Office (57) ABSTRACT

A detection chip is provided. The detection chip includes a substrate, an active reagent, a hydrophilic droplet and a lipophilic substance. The substrate includes a first containing slot, wherein the first containing slot includes a first space and a second space adjacent to each other. The active reagent is disposed in the first space of the first containing slot. The hydrophilic droplet is disposed in the second space of the first containing slot. The lipophilic substance is disposed in the first containing slot, wherein the lipophilic substance is immiscible to the active reagent and the hydrophilic droplet, and separates the active reagent from the hydrophilic droplet.

4 Claims, 8 Drawing Sheets

(52) U.S. Cl.
CPC .... *B01L2300/0867* (2013.01); *B01L 2300/161* (2013.01); *B01L 2400/043* (2013.01); *B01L 2400/0421* (2013.01); *B01L 2400/0427* (2013.01); *Y10T 436/2575* (2015.01)

(56) References Cited

U.S. PATENT DOCUMENTS

| | | | |
|---|---|---|---|
| 5,677,133 | A | 10/1997 | Oberhardt |
| 6,121,055 | A | 9/2000 | Hargreaves |
| 7,906,074 | B2 | 3/2011 | Hong et al. |
| 7,926,514 | B2 | 4/2011 | Park et al. |
| 7,981,385 | B2 | 7/2011 | Park et al. |
| 7,993,828 | B2 | 8/2011 | Gumbrecht et al. |
| 7,998,433 | B2 | 8/2011 | Park et al. |
| 8,088,576 | B2 | 1/2012 | Gumbrecht et al. |
| 8,093,604 | B2 | 1/2012 | Chik et al. |
| 8,187,808 | B2 | 5/2012 | Kelso et al. |
| 8,852,952 | B2 * | 10/2014 | Pollack ............ B01L 3/502715 436/174 |
| 2008/0053205 | A1 * | 3/2008 | Pollack ................ G01N 35/10 73/61.71 |
| 2009/0226911 | A1 | 9/2009 | Mauk et al. |
| 2009/0246782 | A1 * | 10/2009 | Kelso et al. ...................... 435/6 |
| 2010/0282609 | A1 * | 11/2010 | Pollack ................ B01L 3/5027 204/450 |
| 2014/0141409 | A1 * | 5/2014 | Foley .................... B01L 7/525 435/5 |

FOREIGN PATENT DOCUMENTS

| | | |
|---|---|---|
| CN | 101748204 | 6/2010 |
| CN | 102027367 | 4/2011 |
| CN | 102580644 | 7/2012 |
| CN | 102586226 | 7/2012 |
| TW | 221493 | 3/1994 |
| TW | 326075 | 2/1998 |
| TW | 200911375 | 3/2009 |
| TW | 201015059 | 4/2010 |
| TW | I348900 | 9/2011 |
| TW | I350370 | 10/2011 |
| WO | 2006071770 | 7/2006 |

OTHER PUBLICATIONS

Robin Hui Liu, et al., "Self-Contained, Fully Integrated Biochip for Sample Preparation, Polymerase Chain Reaction Amplification, and DNA Microarray Detection," Analytical Chemistry, vol. 76, No. 7, Apr. 1, 2004, pp. 1824-1831.

Alexis F. Sauer-Budge, et al., "Low cost and manufacturable complete microTAS for detecting bacteria," The Royal Society of Chemistry, Jun. 29, 2009, pp. 2803-2810.

Dean Y. Stevens, et al, "Enabling a microfluidic immunoassay for the developing world by integration of on-card dry reagent storage," The Royal Society of Chemistry, Oct. 16, 2008, pp. 2038-2045.

Kameel Abi-Samra, et al., "Infrared controlled waxes for liquid handling and storage on a CD-microfluidic platform," The Royal Society of Chemistry, Nov. 3, 2010, pp. 1-4.

Kunal Sur, et al., "Immiscible Phase Nucleic Acid Purification Eliminates PCR Inhibitors with a Single Pass of Paramagnetic Particles through a Hydrophobic Liquid," Journal of Molecular Diagnostics, vol. 12, No. 5, Sep. 2010, pp. 620-628.

Roger Boden, et al., "On-chip liquid storage and dispensing for lab-on-a-chip applications," Journal of Micromechanics and Microengineering, Jun. 26, 2008, pp. 1-8.

"Office Action of China Counterpart Application," issued on Dec. 1, 2015, p. 1-p. 11, in which the listed references were cited.

* cited by examiner

DETECTION CHIP AND METHOD FOR USING THE SAME

CROSS-REFERENCE TO RELATED APPLICATION

This application claims the priority benefit of Taiwan application serial no. 102124053, filed on Jul. 4, 2013. The entirety of the above-mentioned patent application is hereby incorporated by reference herein and made a part of this specification.

BACKGROUND

1. Technical Field

The technical field relates to a detection chip and a method for using the same, and particularly, to a detection chip capable of storing and reusing a reagent and a method for using the detection chip.

2. Background

In recent years, with the rapid development of biotechnology and the increasing demands for preventive medicine and early diagnosis in medical care, the use of micro-electromechanical system technology for producing biochips has come into attention.

Although current biochip detection has vigorously been developed with different methods, the developments in the preservation and use of reagents are still scanty. In detail, during the general use of the biochip, a variety of different reagents are required to be additionally added into the biological chips. This means that, when using the tiny biochip, a user also needs to prepare a large number of reagents. In addition, under certain circumstances, the aforementioned operation is required to be performed in a laboratory and thus stationary and field uses of the biochip are unable to be effectively developed. Therefore, a detection chip including self-contained reagents and can be quickly reused is urgently in need.

SUMMARY

The detection chip in an exemplary embodiment of the disclosure includes a substrate, an active reagent, a hydrophilic droplet and a lipophilic substance. The substrate includes a first containing slot, wherein the first containing slot includes a first space and a second space adjacent to each other. The active reagent is disposed in the first space of the first containing slot. The hydrophilic droplet is disposed in the second space of the first containing slot. The lipophilic substance is disposed in the first containing slot, wherein the lipophilic substance is immiscible to the active reagent and the hydrophilic droplet, and separates the active reagent from the hydrophilic droplet.

The method for using the detection chip in an exemplary embodiment of the disclosure includes the following steps. The detection chip as described in the above is provided. The lipophilic substance in the detection chip is transformed from solid to liquid. The external force device is being used to enable the hydrophilic droplet or a sample to be in contact with the active reagent, so that the active reagent is dissolved in the hydrophilic droplet or a sample. The hydrophilic droplet, the active reagent and the sample are enabled to be in contact with each other.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
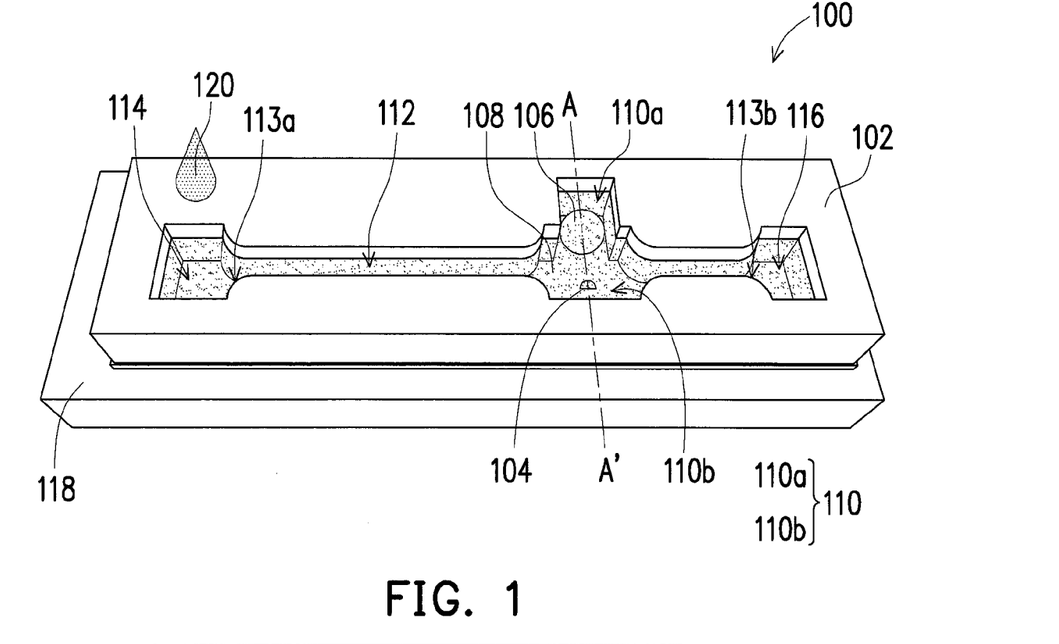
FIG. 1 is a schematic perspective view illustrating a detection chip according to an exemplary embodiment.

FIG. 1 is a schematic perspective view illustrating a detection chip according to an exemplary embodiment. In FIG. 1, a detection chip 100, for example, is a microfluidic chip, and thus the detection chip 100 has elements corresponded to the microfluidic chip, which includes a flow channel 112, an injection slot 114 and a detection slot 116. Certainly, according to an application of the detection chip 100, the detection chip 100 may further include a microsensor (not shown), a microactuator (not shown), a micropump (not shown), a microfluidic mixer (not shown) and so forth. However, the disclosure is not limited thereto. With the descriptions of the detection chip 100 of FIG. 1 below, one of ordinary skills in the art would be able to understand that the detection chip of the disclosure may also be a microarray chip or other types of chip. If the detection chip 100 is a microarray chip or other types of chip, the detection chip 100 would further include elements required by and corresponded to the microarray chip or the other types of chip. Therefore, the detection chip of the disclosure is not limited by the illustration of FIG. 1.

Referring to FIG. 1, the detection chip 100 includes a substrate 102, an active reagent 104, a hydrophilic droplet 106 and a lipophilic substance 108.

The substrate 102 includes a first containing slot 110, and the first containing slot 110 includes a space 110a and a space 110b adjacent to each other. Herein, the substrate 102, for example, is a silicon substrate, a glass substrate, a plastic substrate or other appropriate substrate.

In the present embodiment, the substrate 102 further includes a flow channel 112 connected through with the space 110b of the first containing slot 110, and the flow channel 112 has a starting terminal 113a and a ending terminal 113b relative to the starting terminal 113a. Moreover, in the present embodiment, the substrate 102 further includes an injection slot 114 disposed at the starting terminal 113a of the flow channel 112, and the substrate 102 also includes a detection slot 116 disposed at the ending terminal 113b of the flow channel 112. One of ordinary skills in the art should be able to understand that, a sample 120 may be added from the injection slot 114 into the detection chip 100; and accordingly to actual detection requirements, the sample 120 moved into the detection slot 116 may be detected with different detection systems. However, in other embodiments, the substrate 102 may exclude the detection slot 116. Namely, the detection chip 100 may obtain a detection result without the detection slot 116. A method for forming the flow channel 112, the first containing slot 110, the injection slot 114 and the detection slot 116 is, for example, lithography and etching process, photolithography technique or other proper processing method.

The active reagent 104 is disposed in the space 110b of the first containing slot 110. In the present embodiment, the active reagent 104 may exist in a dry solid state, and may also exist in a liquid state. Namely, the active reagent 104 may be a dry solid active reagent, or a liquid active reagent. More specifically, in biochemical detections, many active reagents 104 stored in the detection chip 100 are preserved in an active state, and as a result, detection activities thereof become vulnerable to decay, and thus a usability of detection chip 100 is reduced. Hence, for reagents that are susceptible to activity decay if being preserved in a solution state, the disclosure may store the reagents in the detection chip 100 as in a powder solid state or a liquid state before activation; so that the time for preserving the reagents in the detection chip 100 is increased. In the present embodiment, the active reagent 104, for example, is an enzyme-containing reagent, an antibody-containing reagent, an antigen-containing reagent, a protein-containing reagent, a nucleotide-containing reagent, a primer-containing reagent or a metal compound-containing reagent.

The hydrophilic droplet 106 is disposed in the space 110a of the first containing slot 110. In the present embodiment, the hydrophilic droplet 106 may dissolve the active reagent 104. Therefore, when the hydrophilic droplet 106 contacts the active reagent 104, the active reagent 104 may be transformed from a preservation state (dry solid or liquid) into a usage state (solution), so as to facilitate the conduct of the detection reaction. In the present embodiment, the hydrophilic droplet 106, for example, is water, a buffer solution, surfactant or a detection reagent containing biomolecule. In addition, if the active reagent 104 is in a condition of having the detection activity due to being activated by other substances, then these substances may also be added into the hydrophilic droplet 106. For instance, when the active reagent 104 is the enzyme-containing reagent, the hydrophilic droplet 106 may be soluble enzyme and a buffer solution for providing an enzyme activation environment after dissolution, or a substance capable of enzyme activation may be added into the hydrophilic droplet 106. Moreover, it is to be noted that, even though in the embodiment illustrated in FIG. 1, the active reagent 104 is disposed in the space 110b, and the hydrophilic droplet 106 is disposed in the space 110a, the disclosure is not limited thereto. In other embodiments, the active reagent 104 may also be disposed in the space 110a, while the hydrophilic droplet 106 is disposed in the space 110b.

The lipophilic substance 108 is disposed in the first containing slot 110, wherein the lipophilic substance 108 is immiscible to the active reagent 104 and the hydrophilic droplet 106, and the lipophilic substance 108 separates the active reagent 104 from the hydrophilic droplet 106. In detail, through the immiscible characteristics of oil and water, an oily environment provided by the lipophilic substance 108 enables the active reagent 104 and the hydrophilic droplet 106 to exist in the detection chip 100 and apart from each other.

According to an exemplary embodiment, the lipophilic substance 108 is in the solid state under a temperature of less than about 10° C., and is in the liquid state under a temperature of about 15 to 30° C. In detail, as described in above, the active reagent 104 and the hydrophilic droplet 106 are spaced by the lipophilic substance 108, and thus when transporting the detection chip 100, the hydrophilic droplet 106 still may move and thereby contacting the active reagent 104. Hence, through the phase transition characteristics of the lipophilic substance 108 under different temperature environments, the hydrophilic droplet 106 may be fixed at a proper position for facilitating the transport when the lipophilic substance 108 is in the solid state. In the present embodiment, the lipophilic substance 108, for example, is a liquid wax. Material properties of the lipophilic substance 108 are not particularly limited as long as the lipophilic substance 108 may be phase changed into solid or liquid under specific environments.

Further, in the present embodiment, in addition to use the aforementioned method of changing the temperature, a method of illumination may also be used to enable the lipophilic substance 108 appeared in the solid state to be transformed into the liquid state, so as to facilitate the subsequent steps. However, the disclosure is not limited thereto, as long as the lipophilic substance 108 can be transformed from the solid state into the liquid state.

Moreover, in the present embodiment, the detection chip 100 further includes an external force device 118 disposed outside of the substrate 102. The external force device 118 is configured to generate an external force to enable the hydrophilic droplet 106 to move towards a specific direction. In the present embodiment, the external force device 118, for example, is an electrical device, a magnetic device or an ultrasonic device. For instance, when the external force device 118 is the magnetic device, the hydrophilic droplet 106 further includes magnetic particles, and thereby the hydrophilic droplet 106 is enabled to move through a magnetic force generated a coil internally built in the force device 118. In FIG. 1, even though the detection chip 100 is illustrated to include the external force device 118 located below the substrate 102, the disclosure is not limited thereto. In other embodiments, the detection chip 100 may include the external force device 118 located at above or below the substrate 102, or may exclude the external force device 118.

Next, a method of using the detection chip of the disclosure is described in detail below.

Figure 2:
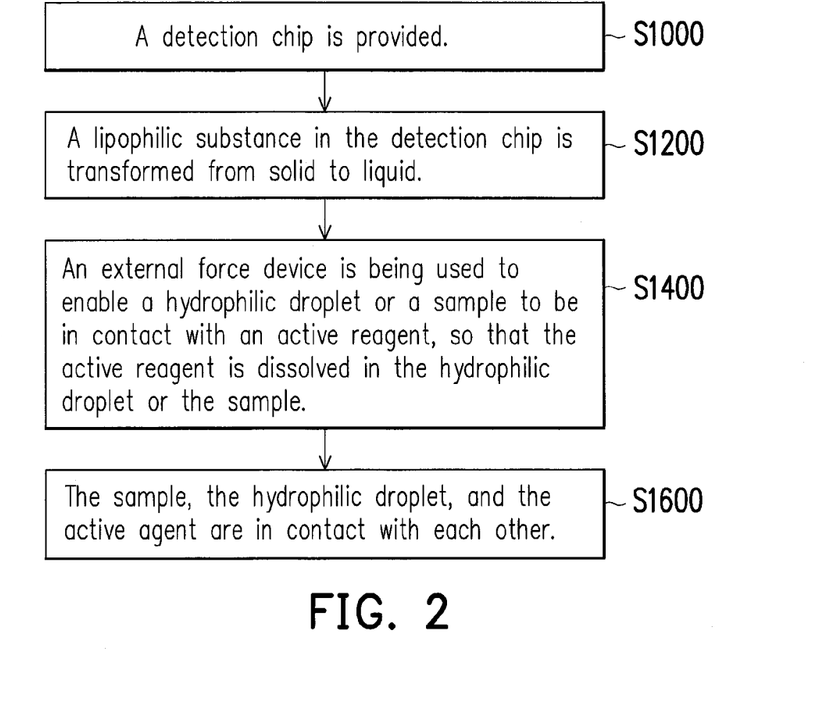
FIG. 2 is a flow chart of a method for using the detection chip according to an exemplary embodiment.

FIG. 2 is a flow chart of a method for using the detection chip according to an exemplary embodiment. Referring to FIG. 2, the method for using the detection chip includes the following steps. A detection chip is provided (step S1000). A lipophilic substance in the detection chip is transformed from solid to liquid (step S1200). An external force device is being used to enable a hydrophilic droplet or a sample to be in contact with an active reagent, so that the active reagent is dissolved in the hydrophilic droplet or a sample (step S1400). The sample, the hydrophilic droplet and the active agent are in contact with each other (step S1600). In the following below, the detection chip 100 of FIG. 1 has been taken as an example for description.

First, in the step S1000, the detection chip of the present embodiment is the detection chip 100. Materials and functions of various elements in the detection chip 100 have already been described in detail in the above embodiment, and thus are not to be repeated herein.

Next, the step S1200 of FIG. 2 is performed. Based on the above description regarding to the lipophilic substance 108 in the detection chip 100, by using the method of changing temperature or illumination, the lipophilic substance 108 appeared in the solid state may be transformed into the liquid state to facilitate the conduct of subsequent steps.

Figure 3A:
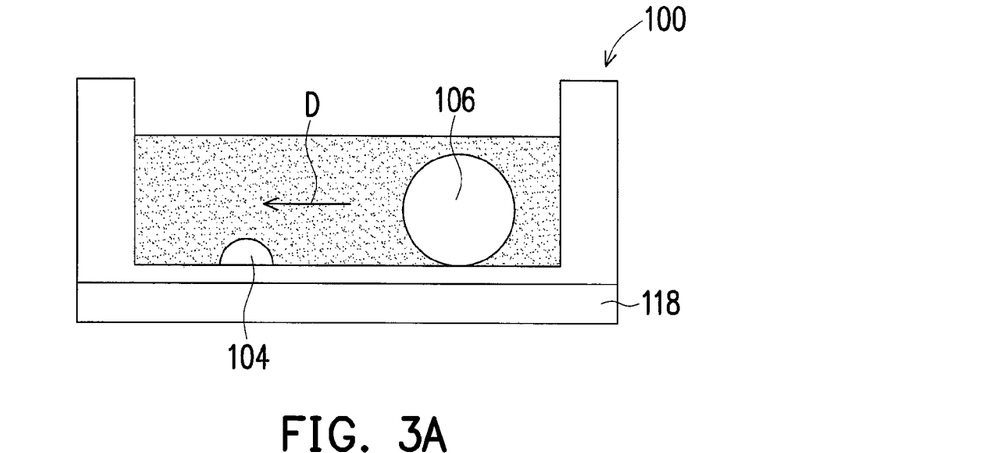
FIG. 3A to FIG. 3C are cross-sectional flow diagrams illustrating a hydrophilic droplet of the detection chip of FIG. 1 coming into contact with an active reagent.
Figure 3B:
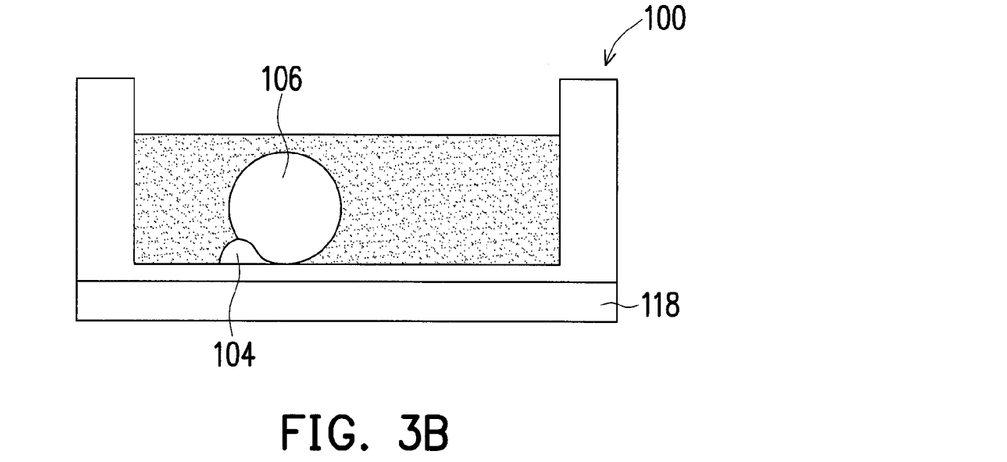
Figure 3C:
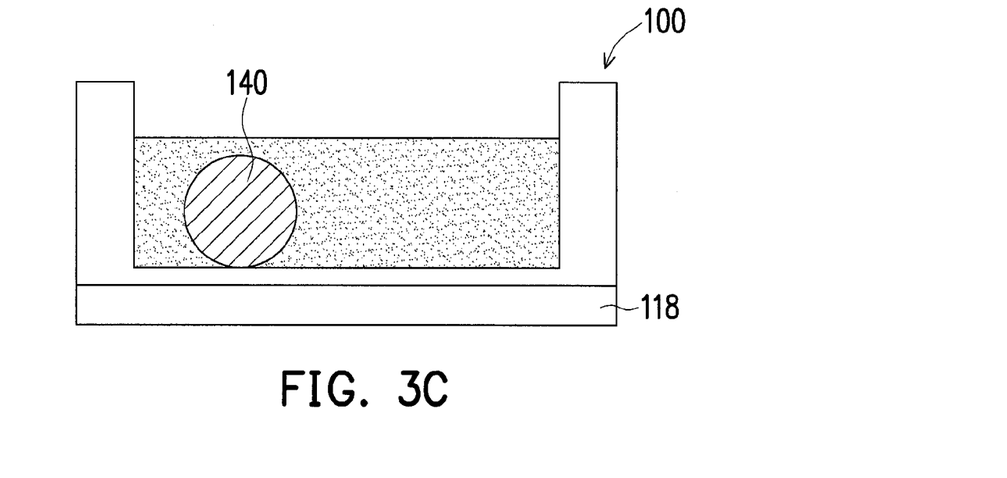

Next, the step S1400, accompanied by FIG. 3A to FIG. 3C, is to be described in detail below; however, the disclosure is not limited to the contents disclosed below.

FIG. 3A to FIG. 3C are cross-sectional flow diagrams illustrating a hydrophilic droplet of the detection chip of FIG. 1 coming into contact with an active reagent, wherein FIG. 3A is a cross-sectional view of a profile line A-A' of FIG. 1.

Firstly, referring to FIG. 3A, in an exemplary embodiment, the external force device 118 is the electrical device, and the external force device 118 applies electric power to the hydrophilic droplet 10, so that the hydrophilic droplet 106, due to electrophoretic force, moves toward the active reagent 104 along a direction D, and thereby comes into contact with the active reagent 104. Next, referring to FIG. 3B to FIG. 3C, after the hydrophilic droplet 106 is in contact with the active reagent 104, the active reagent 104 is dissolved in the hydrophilic droplet 106 to form the first droplet reagent 140.

In the above-mentioned embodiment, the hydrophilic droplet 106 is described with a substance self-containing of specific polar molecules or ionic compounds. However, the disclosure is not limited thereto. Wherein, the above-mentioned process of enabling the hydrophilic droplet 106 to move towards the active reagent 104 via the electrophoretic force may be performed by additionally adding charged particles into the hydrophilic droplet 106. In addition, under the above-mentioned condition that the external force device 118 applies the electric power to the hydrophilic droplet 106, a surface tension of the hydrophilic droplet 106 may further be changed through electro-wetting force, so that the hydrophilic droplet 106 moves toward the active reagent 104 along the direction D. Moreover, in other embodiments, the external force device 118 may also be the ultrasonic device and apply ultrasonic vibrations to the hydrophilic droplet 106, so that the hydrophilic droplet 106 moves toward the active reagent 104 along the direction D, and thereby comes into contact with the active reagent 104.

Moreover, the step S1400 may further be realized through other methods. Namely, in addition to the method disclosed in FIG. 3A to FIG. 3C, the step S1400 may also be performed according to other embodiments, as provided in the following descriptions.

Figure 4A:
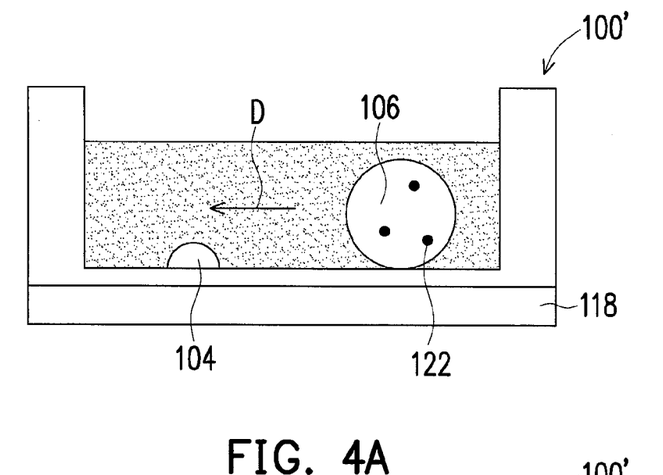
FIG. 4A to FIG. 4C are cross-sectional flow diagrams illustrating a hydrophilic droplet coming into contact with an active reagent according to an exemplary embodiment.
Figure 4B:
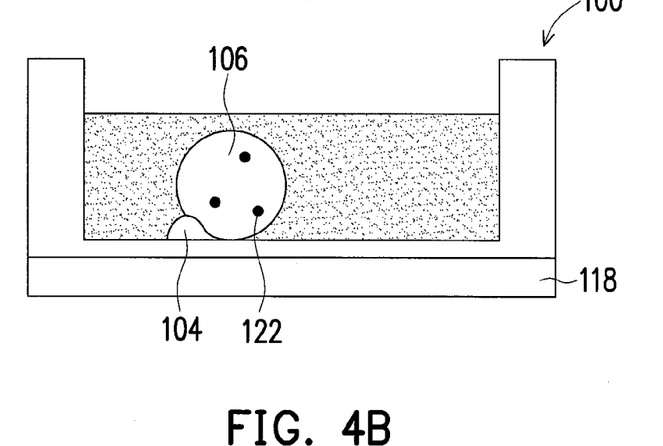
Figure 4C:
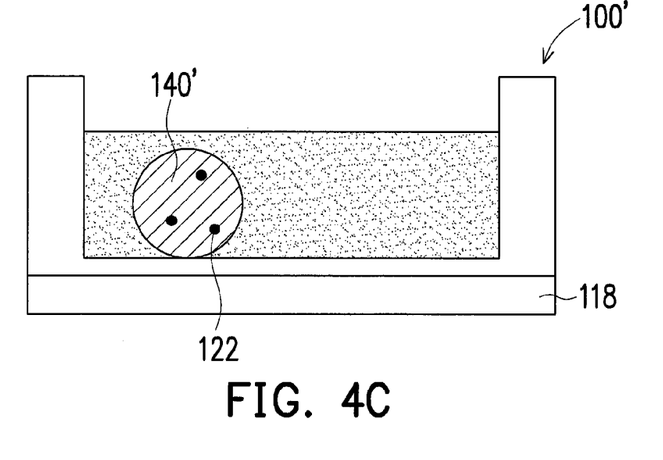

FIG. 4A to FIG. 4C are cross-sectional flow diagrams illustrating a hydrophilic droplet coming into contact with an active reagent according to an exemplary embodiment. Referring to FIG. 4A and FIG. 3A at the same time, a detection chip 100' of this embodiment is similar to the detection chip 100 of FIG. 3A, and thus elements similar to that of FIG. 3A are represented by the same reference numerals. Nevertheless, in the embodiment of FIG. 4A, the hydrophilic droplet 106 further includes magnetic particles 122 and is corresponded to the magnetic particles 122, such that the external force device 118 in this embodiment is the magnetic device.

Referring to FIG. 4A again, the external force device 118 is being used to apply magnetic force to the hydrophilic droplet 106, so that the hydrophilic droplet 106, due to the magnetic force, moves toward the active reagent 104 along the direction D, and thereby comes into contact with the active reagent 104. Next, referring to FIG. 4B to FIG. 4C, after the hydrophilic droplet 106 is in contact with the active reagent 104, the active reagent 104 is dissolved in the hydrophilic droplet 106 to form a first droplet reagent 140'.

Figure 5A:
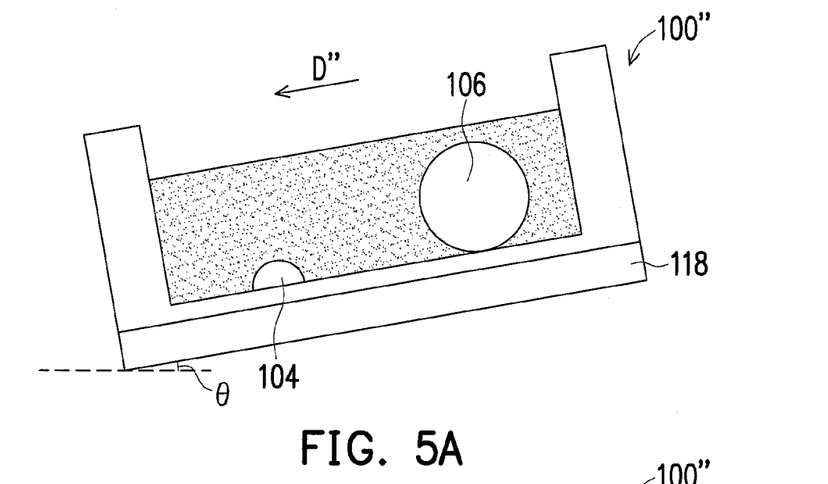
FIG. 5A to FIG. 5C are cross-sectional flow diagrams illustrating a hydrophilic droplet coming into contact with an active reagent according to an exemplary embodiment.
Figure 5B:
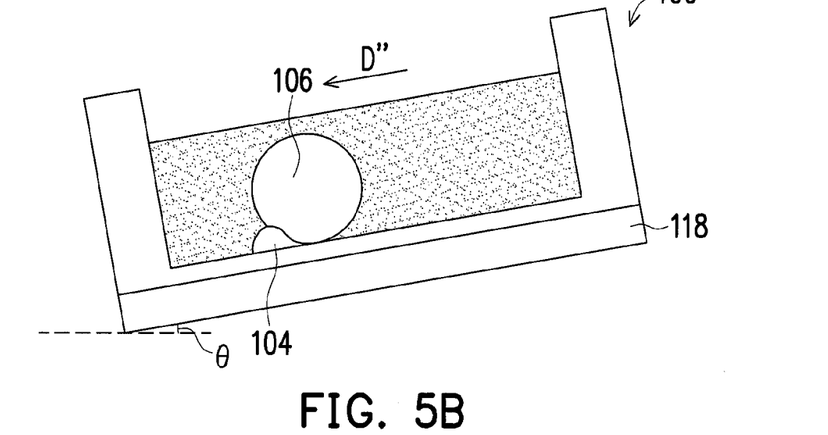
Figure 5C:
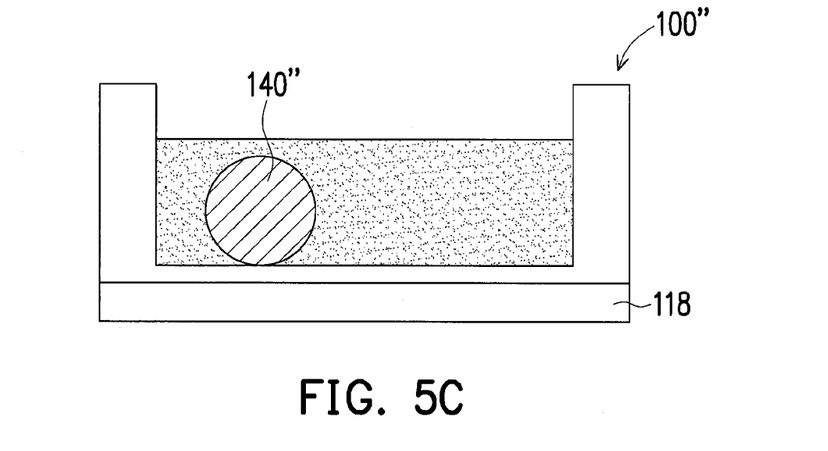

Furthermore, FIG. 5A to FIG. 5C are cross-sectional flow diagrams illustrating a hydrophilic droplet coming into contact with an active reagent according to an exemplary embodiment. Referring to FIG. 5A and FIG. 3A at the same time, a detection chip 100" of this embodiment is similar to the detection chip 100 of FIG. 3A, and thus elements similar to that of FIG. 3A are represented by the same reference numerals.

Firstly, referring to FIG. 5A, in an exemplary embodiment, the external force device 118 is the device tiltable for gravity to take action, and the detection chip 100" may be tilted by an angle θ through the external force device 118; as such, the hydrophilic droplet 106, due to gravitational effect, moves toward the active reagent 104 along a direction D", and thereby comes into contact with the active reagent 104. However, the disclosure is not limited thereto. In other embodiments, a user may enable the detection chip 100" to tilt by the angle θ through both hands thereof, so as to achieve the same result described in above.

Next, referring to FIG. 5B to FIG. 5C, after the hydrophilic droplet 106 is in contact with the active reagent 104, the active reagent 104 is dissolved in the hydrophilic droplet 106 to form a first droplet reagent 140".

Figure 6:
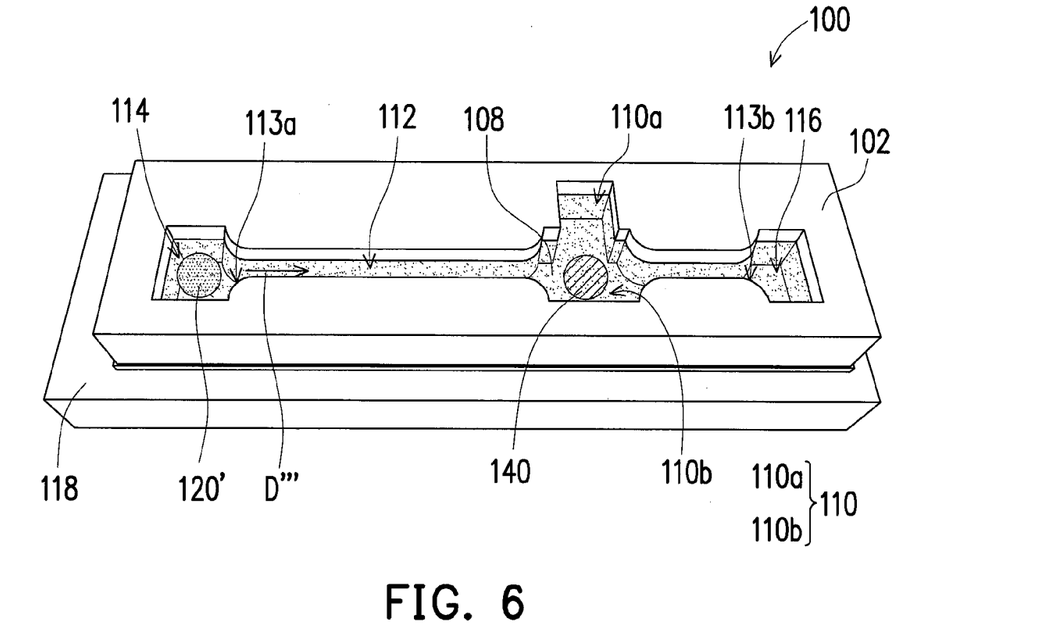
FIG. 6 is a schematic perspective view illustrating a sample coming into contact with a first droplet reagent according to an exemplary embodiment.

After the active reagent 104 is enabled to be dissolved in the hydrophilic droplet 106 to form the first droplet reagent (viz. the step S1400 of FIG. 2) according to the above-mentioned method, the step S1600 of FIG. 2 is then performed. Referring to FIG. 2, FIG. 3C and FIG. 6 at the same time for describing the step S1600. A sample 120' may be added from the injection slot 114 and moves toward the first droplet reagent 140 along a direction D''' through the flow channel 112, so as to be in contact with the first droplet reagent 140. According to the above descriptions, one of ordinary skills in the art would be able to understand that the sample 120' may also contact the first droplet reagent 140' or the first droplet reagent 140" with the same manner. Moreover, in this embodiment, after the sample is in contact with the first droplet reagent 140, the detection result may be obtained from the containing slot 110 through visual observation or other observation means.

Figure 7:
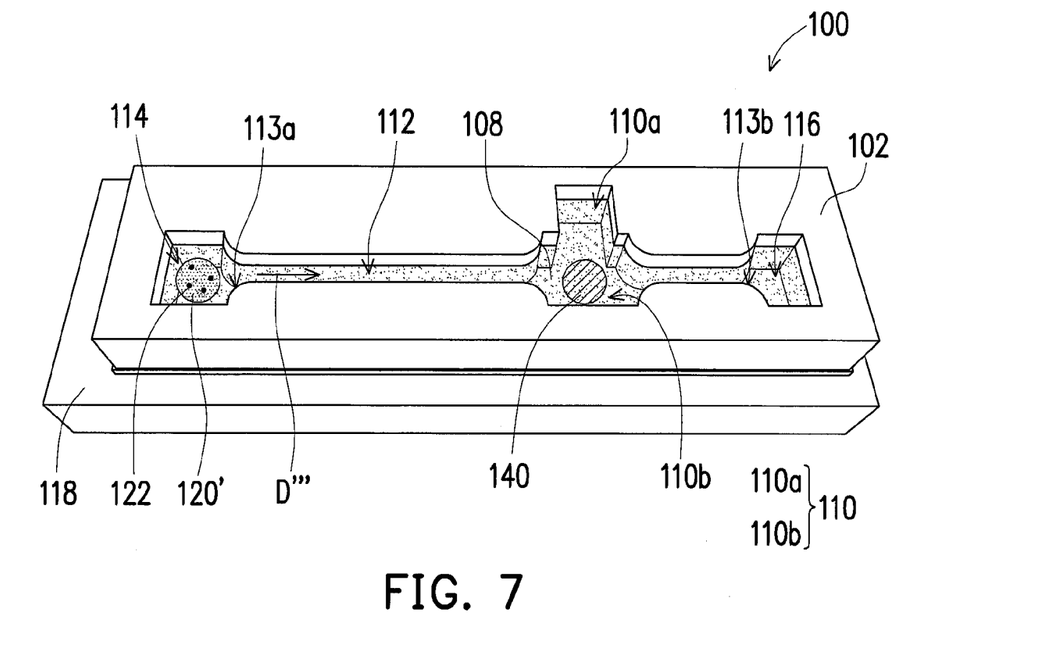
FIG. 7 is a schematic perspective view illustrating a sample coming into contact with a first droplet reagent according to another embodiment.

Moreover, based on the above-disclosed contents regarding to the use of the external force device to enable the hydrophilic droplet or a sample to be in contact with the active reagent, one of ordinary skills in the art should be able to understand that the sample 120' may also be in contact with the first droplet reagent 140, 140' or 140" through similar means. For instance, in an exemplary embodiment, the sample 120' may further include the magnetic particles 122 and is corresponded to the magnetic particles 122, and the external force device 118 in this embodiment is the magnetic device. More specifically, referring to FIG. 7, the external force device 118 is being used to apply the magnetic force to the sample 120', so that the sample 120', due to the magnetic force, moves toward the first droplet reagent 140 along a direction D''' through the flow channel 112, and thereby comes into contact with the first droplet reagent 140.

Moreover, the step S1600 may further be realized through other methods. Namely, in addition to the method disclosed in FIG. 6, the step S1600 may also be performed through enabling the first droplet reagent (e.g., the first droplet reagent 140, 140' or 140") to move towards the sample (e.g., the sample 120'), as described in detail below.

Figure 8:
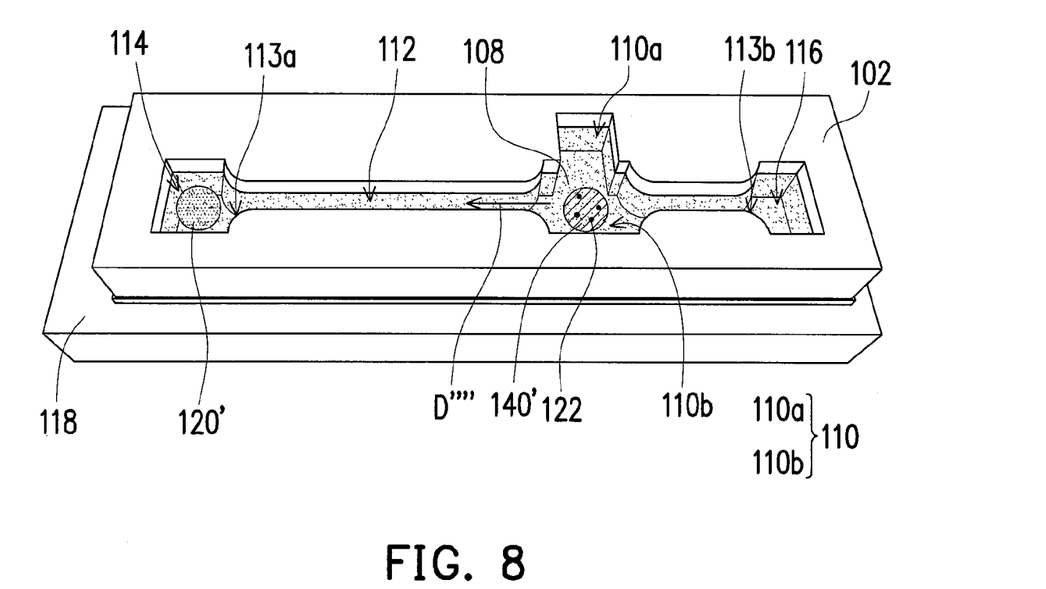
FIG. 8 is a schematic perspective view illustrating a sample coming into contact with a first droplet reagent according to yet another embodiment.

FIG. 8 is a schematic perspective view illustrating a sample coming into contact with a first droplet reagent according to yet another embodiment. Noteworthily, the embodiment of FIG. 8 has taken the first droplet reagent 140' as an example for description. As a result, based on the above-disclosed contents regarding to FIG. 4A to FIG. 4C, the first droplet reagent 140' includes the magnetic particles 122 therein and is corresponded to the magnetic particles 122, and the external force device 118 is this embodiment is the magnetic device. In detail, referring to FIG. 8, the external force device 118 is being used to apply the magnetic force to the first droplet reagent 140', so that the first droplet reagent 140', due to the magnetic force, moves toward the sample 120' along a direction D"" through the flow channel 112, and thereby comes into contact with the sample 120'.

In another embodiment, after the step S1600 is performed, the sample is enabled to move to the detection slot 116 through the flow channel 112, and a detection signal is obtained by performing a detection step from the detection slot 116. The detection step, for example, may be performed through an electrochemical method, a fluorescence detection method, a cold light detection method, an absorption spectroscopy, a reflectance spectroscopy, a mass spectrometry analysis or so forth.

According to the above-mentioned embodiments, the detection chip of the disclosure has been stored with the active reagent 104 and the hydrophilic droplet 106 therein, and the active reagent 104 may be reused through simple operations. Therefore, no additional reaction reagent is required to be added during a performance of the detection, and thereby a convenience of using the detection chip is improved.

Figure 9:
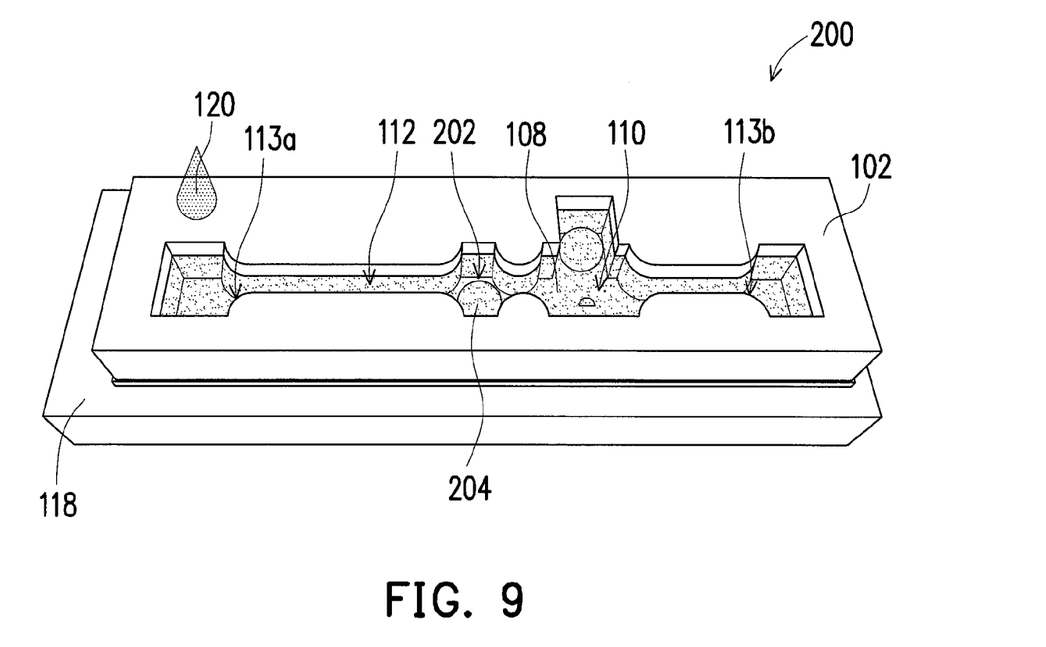
FIG. 9 is a schematic perspective view illustrating a detection chip according to another embodiment.

FIG. 9 is a schematic perspective view illustrating a detection chip according to another embodiment. Referring to FIG. 9 and FIG. 1 at the same time, a detection chip 200 of this embodiment is similar to the detection chip 100 of FIG. 1, and thus elements similar to that of FIG. 1 are represented by the same reference numerals and detailed descriptions are not to be repeated. Differences between the detection chip 200 of FIG. 9 and the detection chip 100 of FIG. 1 are merely that: the substrate 102 further includes a second containing slot 202 connected through with the flow channel 112, the second containing slot 202 further includes a second droplet reagent 204 configured therein, and the second droplet reagent 204 is immiscible to the lipophilic substance 108. In detail, as the second droplet reagent 204 is not susceptible to loss a detection activity thereof when being preserved in the solution state, the second droplet reagent 204 may directly be configured in the second containing slot 202 of the detection chip 200. The second droplet reagent 204, for example, is water, a buffer solution, an alcohol molecule or a surfactant.

Moreover, even though the detection chip 100 has been taken in the above descriptions for illustrating the method for using the detection chip of the disclosure, one of the ordinary skills in the art should be able to understand a method for using the detection chip 200 through the above-disclosed contents. In other words, the method for using the detection chip 200 is similar to the method for using the detection chip 100; namely, the use of the detection chip 200 may also be conducted according to the methods disclosed in FIG. 3A to FIG. 3C, FIG. 4A to FIG. 4C and FIG. 5A to FIG. 5C. Herein, a difference between the method for using the detection chip 200 and the previously described methods is that: before the sample is in contact with the first droplet reagent (e.g., the first droplet reagent 140, 140' or 140"), the sample is firstly in contact with the second droplet reagent 204. Afterward, the detection result may be obtained from the first containing slot 110 and the second containing slot 202 through visual observation or other observation means.

Figure 10:
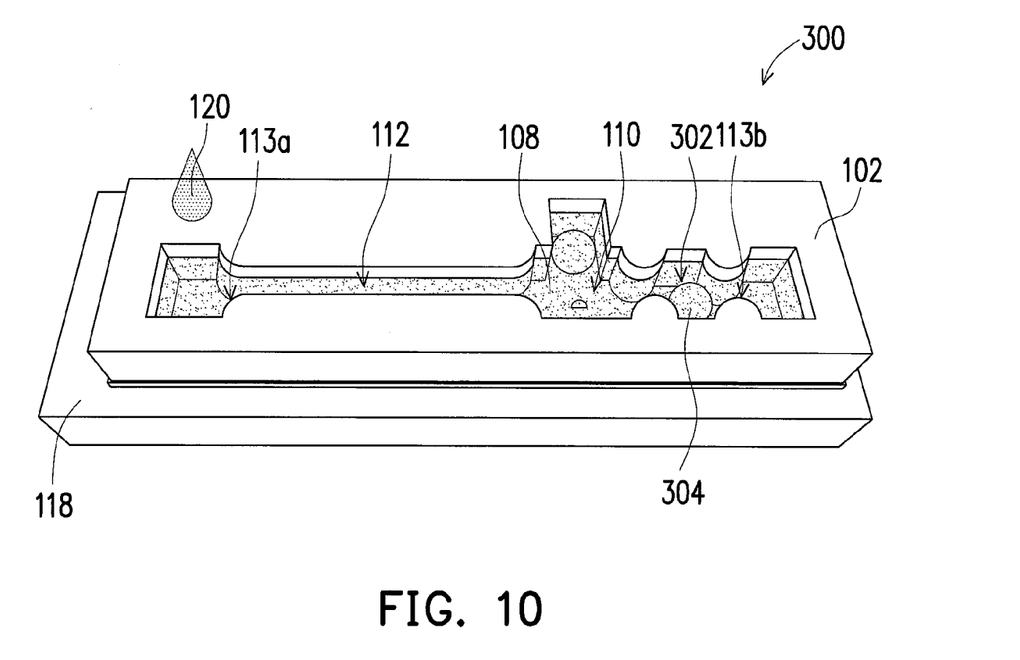
FIG. 10 is a schematic perspective view illustrating a detection chip according to yet another embodiment.

FIG. 10 is a schematic perspective view illustrating a detection chip according to yet another embodiment. Referring to FIG. 10 and FIG. 9 at the same time, a detection chip 300 of the present embodiment is similar to the detection chip 200 of FIG. 9, and thus elements similar to that of FIG. 9 are represented by the same reference numerals and detailed descriptions are not to be repeated. A difference between the detection chip 300 of FIG. 10 and the detection chip 200 of FIG. 9 is merely that: a second containing slot 302 and a second droplet reagent 304 configured within the second containing slot 302 of the embodiment illustrated by FIG. 10 are disposed nearby the ending terminal 113b of the flow channel 112, whereas the second containing slot 202 and the second droplet reagent 204 of FIG. 9 are disposed nearby the starting terminal 113a of the flow channel 112.

Similarly, even though the detection chip 100 has been taken in the above descriptions for illustrating the method for using the detection chip of the disclosure, one of the ordinary skills in the art should be able to understand a method for using the detection chip 300 of FIG. 10 through the above-disclosed contents. In other words, the method for using the detection chip 300 is similar to the method for using the detection chip 100; namely, the use of the detection chip 300 may also be conducted according to the methods disclosed in FIG. 3A to FIG. 3C, FIG. 4A to FIG. 4C and FIG. 5A to FIG. 5C. Herein, a difference between the method for using the detection chip 300 and the previously described methods is that: in the embodiment illustrated by FIG. 10, after the sample is in contact with the first droplet reagent (e.g., the first droplet reagent 140, 140' or 140"), the sample further comes into contact with the second droplet reagent 304. Afterward, the detection result may be obtained from the first containing slot 110 and the second containing slot 302 through visual observation or other observation means.

Figure 11:
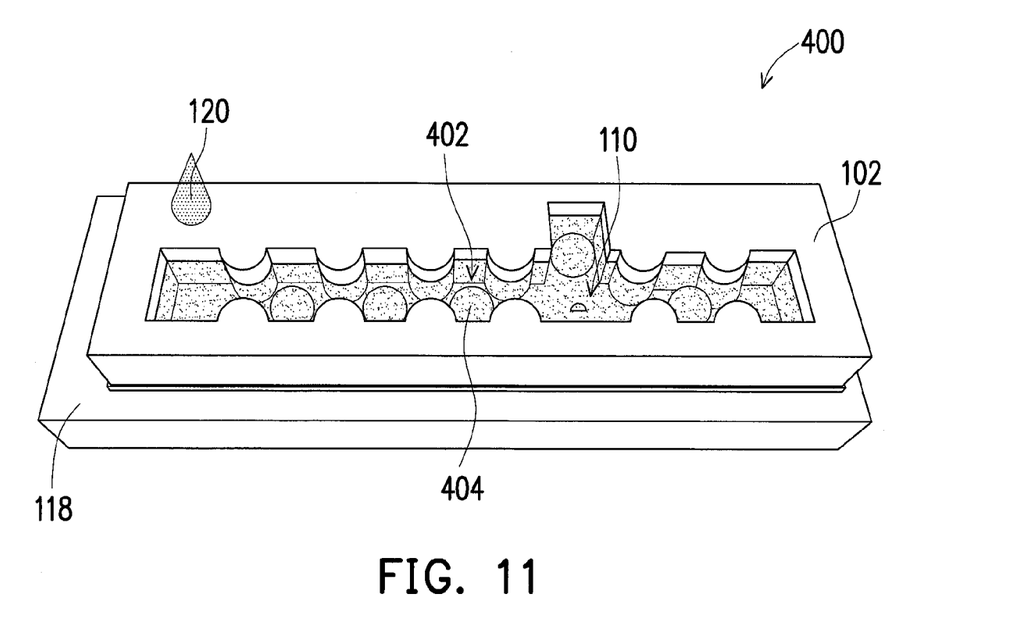
FIG. 11 is a schematic perspective view illustrating a detection chip according to yet another embodiment.

FIG. 11 is a schematic perspective view illustrating a detection chip according to yet another embodiment. Referring to FIG. 11 and FIG. 9 at the same time, a detection chip 400 of the present embodiment is similar to the detection chip 200 of FIG. 9, and thus elements similar to that of FIG. 9 are represented by the same reference numerals and detailed descriptions are not to be repeated. Differences between the detection chip 400 of this embodiment and the detection chip 200 of FIG. 9 are merely that: the substrate 102 of FIG. 11 includes a plurality of second containing slots 402, and each second containing slot 402 is correspondingly configured with a second droplet reagent 404, wherein types of the second droplet reagents 404 may be the same or different from each other. Moreover, in FIG. 11, even through the amount of the second containing slots 402 has been illustrated as four; the disclosure is not limited thereto.

Similarly, even though the detection chip 100 has been taken in the above descriptions for illustrating the method for using the detection chip of the disclosure, one of the ordinary skills in the art should be able to understand a method for using the detection chip 400 of FIG. 11 through the above-disclosed contents. In other words, the method for using the detection chip 400 is similar to the method for using the detection chip 100; namely, the use of the detection chip 400 may also be conducted according to the methods disclosed in FIG. 3A to FIG. 3C, FIG. 4A to FIG. 4C and FIG. 5A to FIG. 5C. Herein, a difference between the method for using the detection chip 400 and the previously described methods is that: in the embodiment illustrated by FIG. 11, the sample, in addition to being in contact with the first droplet reagent (e.g., the first droplet reagent 140,140' or 140"), is further contact with the second droplet reagents 404. Afterward, the detection result may be obtained from the first containing slot 110 and the second containing slots 402 through visual observation or other observation means.

Figure 12:
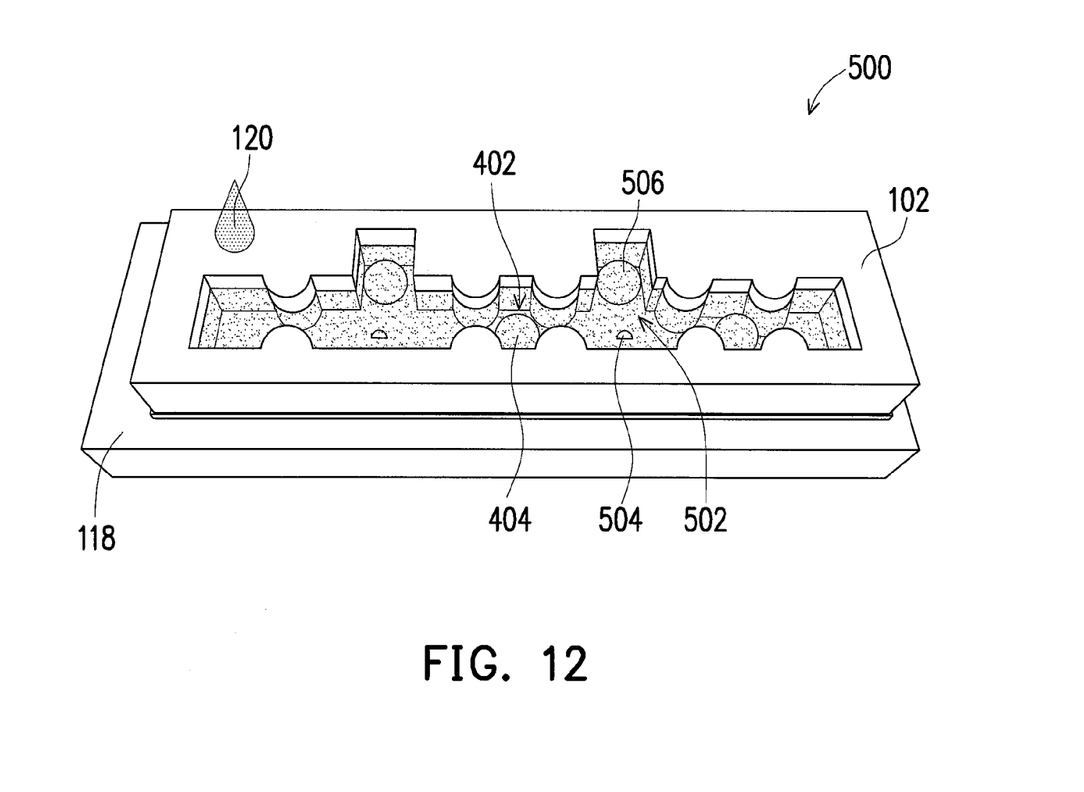
FIG. 12 is a schematic perspective view illustrating a detection chip according to a further exemplary embodiment.

FIG. 12 is a schematic perspective view illustrating a detection chip according to a further exemplary embodiment. Referring to FIG. 12 and FIG. 11 at the same time, a detection chip 500 of the present embodiment is similar to the detection chip 400 of FIG. 11, and thus elements similar to that of FIG. 11 are represented by the same reference numerals and detailed descriptions are not to be repeated. Differences between the detection chip 500 of the present embodiment and the detection chip 400 of FIG. 11 are merely that: the substrate 102 of FIG. 500 includes a plurality of first containing slots 502, and each first containing slot 502 is correspondingly configured with an active reagent 504 and a first droplet reagent 506, wherein types of the active reagent 504 may be the same or different from each other, and types of the first droplet reagent 506 may be the same or different from each other. Moreover, in FIG. 12, even through the amount of the first containing slots 502 has been illustrated as two and the amount of the second containing slot 402 has been illustrated as two, the disclosure is not limited thereto.

Similarly, even though the detection chip 100 has been taken in the above descriptions for illustrating the method for using the detection chip of the disclosure, one of the ordinary skills in the art should be able to understand a method for using the detection chip 500 of FIG. 12 through the above-disclosed contents. In other words, the method for using the detection chip 500 is similar to the method for using the detection chip 100; namely, the use of the detection chip 500 may also be conducted according to the methods disclosed in FIG. 3A to FIG. 3C, FIG. 4A to FIG. 4C and FIG. 5A to FIG. 5C. Herein, a difference between the method for using the detection chip 500 and the previously described methods is that: in the embodiment illustrated by FIG. 12, the sample may sequentially be in contact with the first droplet reagent (e.g., the first droplet reagent 140,140' or 140") and the second droplet reagents 404, wherein the first droplet reagent is formed by contacting the active reagents 504 with the first droplet reagents 506. Afterward, the detection result may be obtained from the first containing slot 110 and the second containing slots 402 through visual observation or other observation means.

According to another embodiment, the external force device 118 can also be used to enable the sample 120 to be in contact with the active reagent 504 (or the active reagent 104 shown in FIG. 1), so that the active reagent 504 (or the active reagent 104 shown in FIG. 1) is dissolved in the sample 120 to form a droplet reagent. After that, the hydrophilic droplet and the droplet reagent formed from the active reagent 504 (or the active reagent 104 shown in FIG. 1) and the sample 120 are enabled to be in contact with each other.

It can be known from the embodiments depicted by FIG. 9 to FIG. 12, the detection chip provided in the aforementioned embodiments may adjust the arrangement thereof according to different detection requirements, and thus the detection chip and method for using the detection chip of the disclosure may be applied in many fields.

In summary, the active regent and the hydrophilic droplet capable of dissolving the active reagent are properly stored within the detection chip provided in the aforementioned embodiments. In addition, the detection chip provided in the aforementioned embodiments may enable the active reagent to be reused through simpler operations, and thus no additional reaction reagent is required to be added during the performance of the detection, thereby improving a convenience of using the detection chip. Moreover, the detection chip provided in the aforementioned embodiments may adjust the arrangement thereof, the method for using same and the types of the reagent according to the different detection requirements, and thus the detection chip may be applied in a variety of applications.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for using a detection chip, comprising:
   providing a detection chip, wherein the detection chip comprising:
      a substrate, comprising a first containing slot, wherein the first containing slot comprises a first space and a second space adjacent to each other;
      an active reagent, disposed in the first space of the first containing slot;
      a hydrophilic droplet, disposed in the second space of the first containing slot, wherein the hydrophilic droplet comprises magnetic particles therein; and
      a lipophilic substance, disposed in the first containing slot, wherein the lipophilic substance is immiscible to the active reagent and the hydrophilic droplet, and separates the active reagent from the hydrophilic droplet;
   transforming the lipophilic substance in the detection chip from solid to liquid;
   using an external force device to enable the hydrophilic droplet to be in contact with the active reagent, so that the active reagent is dissolved in the hydrophilic droplet to form a first droplet reagent, wherein the external force device is the magnetic device, so that the hydrophilic droplet is enabled to move towards the active reagent due to magnetic force via the magnetic device; and
   enabling a sample to be in contact with the first droplet reagent.

2. The method for using the detection chip as recited in claim 1, wherein the substrate further comprises a second containing slot connected through with the first containing slot, the second containing slot further comprises a second droplet reagent configured therein, the second droplet reagent is immiscible to the lipophilic substance, and the sample contacts the second droplet reagent before or after contacting the first droplet reagent.

3. The method for using the detection chip as recited in claim 1, wherein the sample further comprises magnetic particles.

4. The method for using the detection chip as recited in claim 1, wherein the hydrophilic droplet is in contact with the active reagent on the same plane.

* * * * *